US00PP32071P2

(12) United States Plant Patent
Hoogkamp

(10) Patent No.: US PP32,071 P2
(45) Date of Patent: Aug. 11, 2020

(54) ***CURCUMA* PLANT NAMED 'CURHONIMP'**

(50) Latin Name: *Curcuma alismatifolia*
Varietal Denomination: Curhonimp

(71) Applicant: Timothy Johan Herman Hoogkamp, Doetinchem (NL)

(72) Inventor: Timothy Johan Herman Hoogkamp, Doetinchem (NL)

(73) Assignee: Nubilus B.V., Naaldwijk (NL)

( * ) Notice: Subject to any disclaimer, the term of this patent is extended or adjusted under 35 U.S.C. 154(b) by 0 days.

(21) Appl. No.: 16/501,650

(22) Filed: May 16, 2019

(51) Int. Cl.
*A01H 5/02* (2018.01)
*A01H 6/00* (2018.01)

(52) U.S. Cl.
USPC ..... Plt./421

(58) Field of Classification Search
USPC ..... Plt./421
See application file for complete search history.

*Primary Examiner* — Susan McCormick Ewoldt
(74) *Attorney, Agent, or Firm* — C. A. Whealy

(57) ABSTRACT

A new and distinct cultivar of *Curcuma* plant named 'Curhonimp', characterized by its upright plant habit with outwardly arching leaves; moderately vigorous growth habit; freely clumping growth habit; relatively broad leaves; freely flowering habit; and inflorescences with white and light purple-colored upper flower bracts with yellow green-colored apices positioned above the foliar plane on strong and erect peduncles.

2 Drawing Sheets

Botanical designation: *Curcuma alismatifolia.*
Cultivar denomination: 'CURHONIMP'.

BACKGROUND OF THE INVENTION

The present invention relates to a new and distinct cultivar of *Curcuma* plant, botanically known as *Curcuma alismatifolia* and hereinafter referred to by the name 'Curhonimp'.

The new *Curcuma* plant is a product of a controlled breeding program conducted by the Inventor in Naaldwijk, The Netherlands. The objective of the breeding program is to create new *Curcuma* plants that have uniform plant habit, good container performance and attractive inflorescence coloration.

The new *Curcuma* is a naturally-occurring whole plant mutation of *Curcuma alismatifolia* 'Curhonibo', not patented. The new *Curcuma* plant was discovered and selected by the Inventor as a single flowering plant within a population of plants of 'Curhonibo' in a controlled greenhouse environment in Naaldwijk, The Netherlands in June, 2016.

Asexual reproduction of the new *Curcuma* plant by axillary bud meristem culture in a controlled environment in Naaldwijk, The Netherlands since July, 2016 has shown that the unique features of this new *Curcuma* plant are stable and reproduced true to type in successive generations of asexual reproduction.

SUMMARY OF THE INVENTION

Plants of the new *Curcuma* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Curhonimp'. These characteristics in combination distinguish 'Curhonimp' as a new and distinct *Curcuma* plant:

1. Upright plant habit with outwardly arching leaves.
2. Moderately vigorous growth habit.
3. Freely clumping growth habit.
4. Relatively broad leaves.
5. Freely flowering habit.
6. Inflorescences with white and light purple-colored upper flower bracts with yellow green-colored apices positioned above the foliar plane on strong and erect peduncles.

Plants of the new *Curcuma* differ from plants of the mutation plant, 'Curhonibo', in the following characteristics:

1. Plants of the new *Curcuma* are more freely clumping than plants of 'Curhonibo'.
2. Plants of the new *Curcuma* have more upper flower bracts as plants of 'Curhonibo'.
3. Plants of the new *Curcuma* have white to light purple-colored upper flower bracts whereas plants of 'Curhonibo' have light blue violet-colored upper flower bracts.

Plants of the new *Curcuma* can also be compared to plants of *Curcuma alismatifolia* 'Curalimei', disclosed in U.S. Plant Pat. No. 25,124. In side-by-side comparisons plants of the new *Curcuma* differ from plants of 'Curalimei' in the following characteristics:

1. Plants of the new *Curcuma* are more freely clumping than plants of 'Curalimei'.
2. Leaves of plants of the new *Curcuma* are broader than leaves of plants of 'Curalimei'.
3. Plants of the new *Curcuma* have yellow green and greyed purple-colored lower flower bracts whereas plants of 'Curalimei' have green-colored lower flower bracts.

BRIEF DESCRIPTION OF THE PHOTOGRAPHS

The accompanying photographs illustrate the overall appearance of the new *Curcuma* plant showing the colors as true as it is reasonably possible to obtain in colored reproductions of this type. Colors in the photographs may differ slightly from the color values cited in the detailed botanical description which accurately describe the colors of the new *Curcuma* plant.

The photograph on the first sheet is a side perspective view of a typical plant of 'Curhonimp' grown in a container.

The photograph on the second sheet is a close-up view of a typical inflorescence of 'Curhonimp'.

DETAILED BOTANICAL DESCRIPTION

The aforementioned photographs and following observations and measurements describe plants grown during the spring in 13-cm containers in a glass-covered greenhouse in Naaldwijk, The Netherlands and under cultural practices typical of commercial *Curcuma* production. During the production of the plants, day temperatures ranged from 22° C. to 25° C., night temperatures ranged from 20° C. to 22° C. and light levels averaged 55 kilolux. Plants were 14 weeks old when the photographs and the detailed description were taken. In the following description, color references are made to The Royal Horticultural Society Colour Chart, 2015 Edition, except where general terms of ordinary dictionary significance are used.

Botanical classification: *Curcuma alismatifolia* 'Curhonimp'.

Parentage: Naturally-occurring whole plant mutation of *Curcuma alismatifolia* 'Curhonibo', not patented.

Propagation:

*Type*.—By axillary bud meristem culture.

*Time to initiate roots*.—About ten days at temperatures about 23° C.

*Time to produce a rooted young plant*.—About 28 to 30 days at temperatures about 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately branching, medium density.

Plant description:

*Plant and growth habit*.—Upright plant habit with outwardly arching leaves; overall shape, broadly obovate; freely clumping habit with about seven basal shoots forming per plant; moderately vigorous growth habit and moderate growth rate.

*Plant height* (*soil level to top of inflorescences*).—About 49.5 cm.

*Plant diameter*.—About 41.6 cm.

Leaf description:

*Leaf arrangement*.—Alternate; simple.

*Length, fully expanded*.—About 28.6 cm.

*Width, fully expanded*.—About 10.3 cm.

*Shape*.—Narrowly ovate.

*Apex*.—Apiculate.

*Base*.—Attenuate, sheathing.

*Margin*.—Entire; unlobed.

*Venation*.—Parallel.

*Aspect*.—Initially upright, then outwardly arching.

*Texture and luster, upper and lower surfaces*.—Smooth, glabrous; non-rugose; matte.

*Color*.—Developing leaves, upper surface: Close to between 143C and 144A. Developing leaves, lower surface: Close to between 138B and 143C. Fully expanded leaves, upper surface: Close to 137B; venation, close to 138A. Fully expanded leaves, lower surface: Close to between 137C and 191A; venation, close to between 137C and 191A.

*Leaf sheaths*.—Length: About 15.7 cm. Width: About 1.3 cm. Texture and luster, upper surface: Smooth, glabrous; glossy. Texture and luster, lower surface: Smooth, glabrous; slightly glossy. Color, upper surface: Close to 146A; towards the margins, close to 146B; edges, close to 157D; venation, close to 147A. Color, lower surface: Close to 147A; towards the margins, close to 146C; edges, close to 157D; venation, close to 147A.

Inflorescence description:

*Arrangement*.—Upright terminal spike inflorescences developing directly from the basal shoots with showy upper flower bracts; typically each spike with about 15 clusters each with about five flowers; about 75 flowers developing per plant at one time.

*Time to flower*.—In The Netherlands, plants flower from summer into autumn; flowering continuous during this period; plants begin flowering about ten weeks after planting.

*Flower longevity*.—Flowers last about three days on the plant; flowers persistent; plants maintain good substance for about 40 days.

*Fragrance*.—Faint; somewhat spicy.

*Flower buds*.—Length: About 1.4 cm. Diameter: About 3 mm. Shape: Oblanceolate. Texture and luster: Smooth, glabrous; moderately glossy. Color: Proximally, close to 157C to 157D; mid-section, close to 154C; distally, close to between 83C and N187B.

*Inflorescence length*.—About 11.7 cm.

*Inflorescence diameter*.—About 7.6 cm.

*Flowers*.—Length: About 2.4 cm. Diameter: About 1.1 cm by 1.2 cm. Flower throat diameter: About 8 mm. Flower tube length: About 1.7 cm. Flower tube diameter: About 3 mm. Shape and arrangement: Zygomorphic with three petals, conspicuous labellum and two lateral corolla lobes (staminodia), fused towards the base; gamosepalous calyx with three sepals.

*Labellum*.—Length: About 2.6 cm. Width: About 1 cm. Shape: Narrowly spatulate; fused at the base. Apex: Emarginate to praemorse. Margins: Entire; slightly undulate. Texture and luster, upper surface: Smooth, glabrous; moderately velvety; matte. Texture and luster, lower surface: Smooth, glabrous; slightly glossy. Color: When opening, upper surface: Close to 83A fading towards the center and base to close to 85B; central narrow stripe, close to 14A; proximal narrow stripes (two), close to 50A. When opening, lower surface: Close to 83B to 83C; towards the margins and apex, close to 83A; towards the center and the base, close to 85D. Fully opened, upper surface: Close to 83A fading towards the center and base to close to 85B; central narrow stripe, close to 14A; proximal narrow stripes (two), close to 50A; venation, close to 83A fading towards the base to close to 85D; color becoming closer to N8OB to N80C with development. Fully opened, lower surface: Close to 83B to 83C; towards the margins and apex, close to 83A; towards the center and the base, close to 85D; venation, similar to lamina colors; color becoming closer to N80B to N80C with development.

*Lateral corolla lobes*.—Length: About 2.6 cm. Width: About 8mm. Shape: Oblanceolate. Apex: Narrowly obtuse. Margins: Entire; slightly undulate. Texture and luster, upper surface: Smooth, glabrous; moderately velvety; matte. Texture and luster, lower surface: Smooth, glabrous; slightly glossy. Color: When opening and fully opened, upper surface: Close to 83A fading towards the base to close to N82C; narrow basal stripe, close to 50A; venation, similar to lamina colors; color becoming closer to N80B to N80C with development. When opening and fully opened, lower surface: Close to 83B to 83C; towards the apex and margins, close to 83A; towards the base, close to 85D; venation, similar to lamina colors; color becoming closer to N80B to N80C with development.

*Petals*.—Length, dorsal petal: About 2.3 cm. Length, lateral petals: About 2.2 cm. Width, dorsal petal: About 7 mm. Width, lateral petals: About 5 mm. Shape, dorsal and lateral petals: Narrowly oblanceolate. Apex, dorsal and lateral petal: Narrowly obtuse. Margins, dorsal and lateral petals: Entire; not undulate. Texture and luster, dorsal and lateral petals, upper surface: Smooth, glabrous; matte. Texture and luster, dorsal and lateral petals, lower surface: Smooth, glabrous; slightly glossy. Color, dorsal and lateral petals: When opening, upper and lower surfaces: Close to N85A fading towards the base to close to N155A. Fully opened, upper and lower surfaces: Close to N85A fading towards the base to close to N155A; venation, similar to lamina colors; color does not change with development. Color, flower throat: Close to 160D; venation, close to 155C. Color, flower tube: Close to 160D; venation, close to 155C.

*Calyx*.—Length: About 9 mm. Diameter: About 4 mm. Quantity of sepals and arrangement: Three in a single whorl; fused at the base. Sepal length: About 9 mm. Sepal width: About 4 mm. Sepal shape: Narrowly obovate. Sepal apex: Bluntly acute. Sepal base: Broadly cuneate. Sepal margin: Entire. Sepal texture and luster, upper and lower surfaces: Smooth, glabrous; moderately glossy. Sepal color: When opening and fully opened, upper surface: Close to NN155A. When opening and fully opened, lower surface: Close to NN155A.

*Upper flower bracts*.—Quantity: About twelve upper bracts per inflorescence. Length: About 4.7 cm. Width: About 2.3 cm. Shape: Elliptic to oblong; slightly concave. Apex: Broadly acute. Base: Cuneate. Margin: Entire; moderately undulate. Texture and luster, upper and lower surfaces: Smooth, glabrous; moderately glossy. Color: Proximal bracts, when opening and fully opened, upper surface: Close to 77D; towards the apex, close to 143C; towards the base, close to 145B; stripes, close to 180B; venation, similar to lamina. Proximal bracts, when opening and fully opened, lower surface: Close to 77D; towards the apex, close to 146A and 146D; towards the base, close to 145A; stripes, close to 180C; venation, similar to lamina. Distal bracts, when opening and fully opened, upper surface: Close to NN155D; towards the apex and base, close to 145C; stripes, close to 180B to 180C; venation, similar to lamina. Distal bracts, when opening and fully opened, lower surface: Close to NN155D; towards the apex and base, close to 145C; stripes, close to 180B to 180C; venation, similar to lamina.

*Lower flower bracts*.—Quantity: About eleven lower bracts per inflorescence. Length: About 3.3 cm. Width: About 3.7 cm. Shape: Broadly obovate to inverted reniform; strongly concave. Apex: Obtuse. Base: Cuneate. Margin: Entire; moderately undulate. Texture and luster, upper and lower surfaces: Smooth, glabrous; moderately glossy. Color: When opening and fully opened, upper surface: Close to 146B to 146C; towards the apex, close to 146A; distal blotch, close to 183C to 183D; venation, similar to lamina. When opening and fully opened, lower surface: Close to 146B; towards the apex, close to 146A; distal blotch, close to 183A and 200A; venation, similar to lamina.

*Peduncles*.—Length: About 38.3 cm. Diameter: About 9 mm. Strength: Strong. Aspect: Erect to about 5° from vertical. Texture and luster: Smooth, glabrous; slightly glossy. Color: Close to 146A.

*Stamens*.—Quantity: Two per flower; fused. Filament length: About 8 mm. Filament diameter: About 4 mm. Filament color: Close to N82C. Anther length: About 4 mm. Anther width: About 1.5 mm. Anther shape: Narrowly oblong. Anther color: Close to NN155A; apex, close to 83C. Pollen amount: Moderate. Pollen color: Close to 155C.

*Pistils*.—Quantity per flower: One. Pistil length: About 2.2 cm. Style length: About 2 cm. Style color: Close to N88C; proximally, close to NN155D. Stigma diameter: About 2 mm. Stigma shape: Cupped. Stigma color: Close to NN155B. Ovary color: Close to 157B.

*Seeds and fruits*.—To date, seed and fruit development have not been observed on plants of the new *Curcuma*.

Pathogen & pest resistance: To date, plants of the new *Curcuma* have not been observed to be resistant to pathogens or pests common to *Curcuma* plants.

Temperature tolerance: Plants of the new *Curcuma* have been observed to be tolerant to temperatures ranging from about 5° C. to about 40° C. and are suitable for USDA Hardiness Zones 10 to 12.

It is claimed:

1. A new and distinct *Curcuma* plant named 'Curhonimp' as illustrated and described.

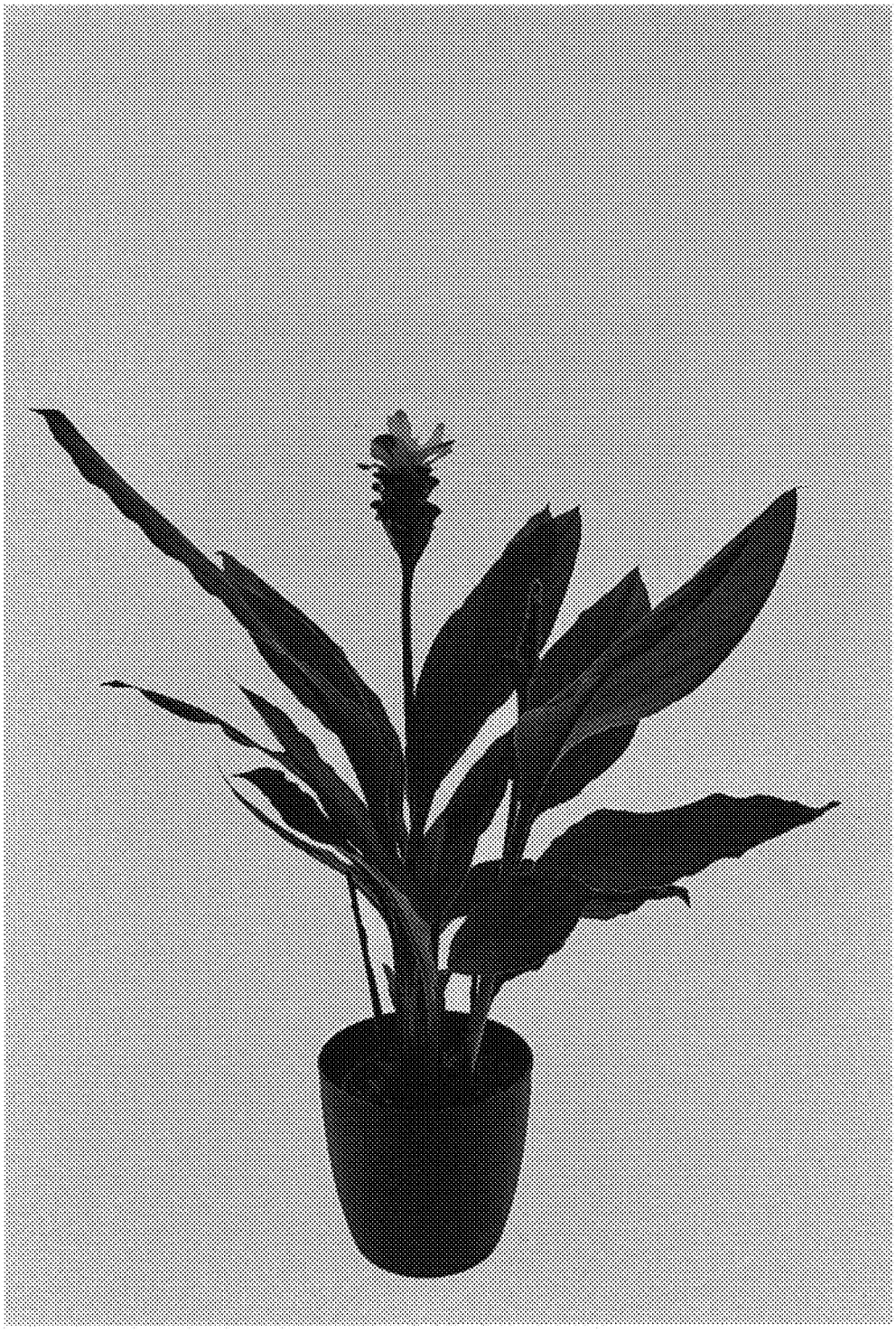

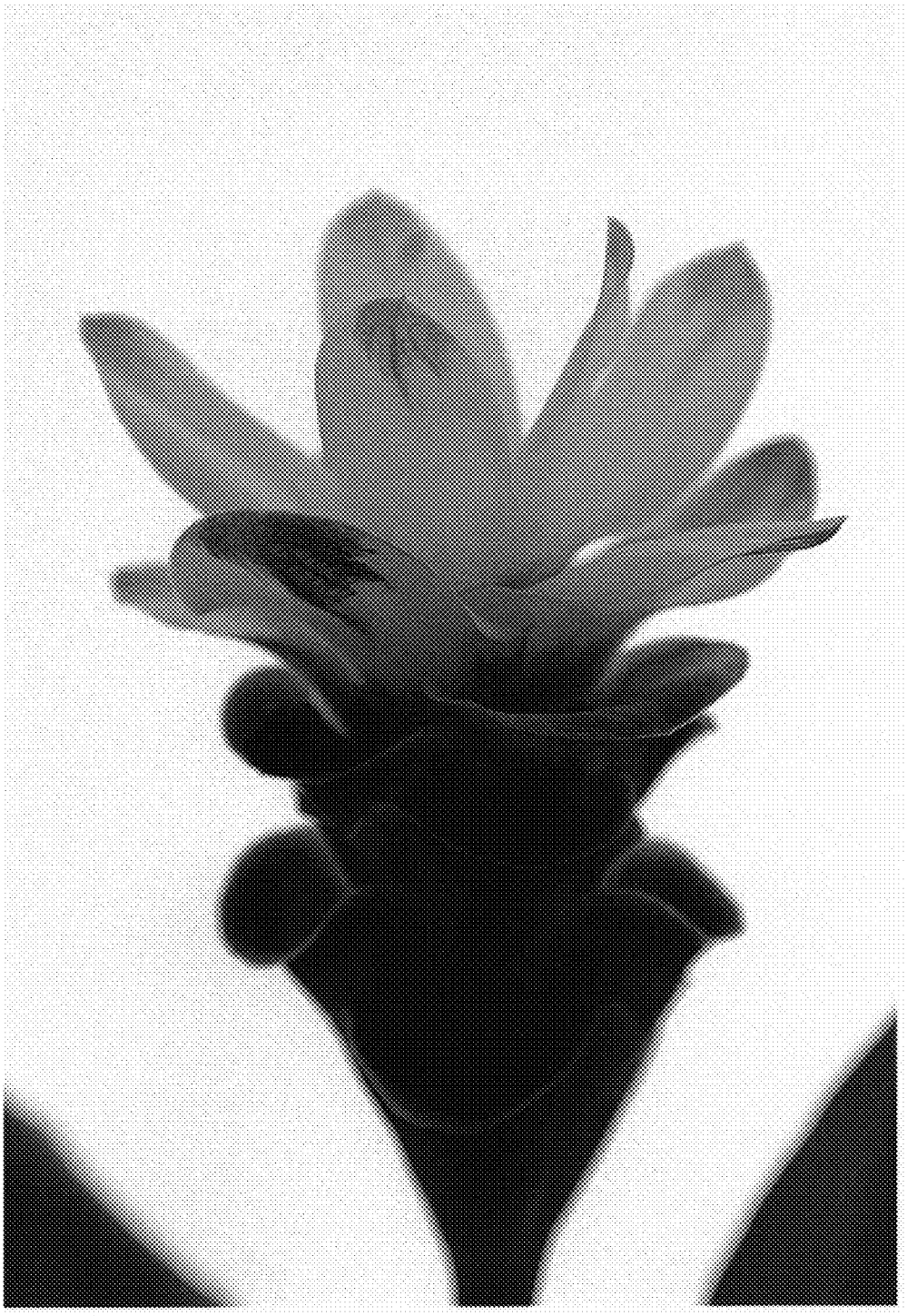

* * * * *